United States Patent [19]

Yasuhisa et al.

[11] Patent Number: 4,888,407

[45] Date of Patent: Dec. 19, 1989

[54] IMIDE COMPOUND AND COMPOSITION CONTAINING THE SAME

[75] Inventors: Saito Yasuhisa, Higashiosaka; Kunimasa Kamio, Suita; Mitsuhiro Shibata, Yao; Katsuya Watanabe, Takatsuki; Yutaka Shiomi, Hirakata; Youichi Ueda, Kashihara, all of Japan

[73] Assignee: Sumitomo Chemical Co., Ltd., Osaka, Japan

[21] Appl. No.: 138,084

[22] Filed: Dec. 28, 1987

[30] Foreign Application Priority Data

Dec. 26, 1986 [JP] Japan .................................. 61-314259
Dec. 26, 1986 [JP] Japan .................................. 61-314260
Jun. 23, 1987 [JP] Japan .................................. 62-157329
Jun. 23, 1987 [JP] Japan .................................. 62-157330
Jun. 23, 1987 [JP] Japan .................................. 62-157331

[51] Int. Cl.$^4$ ...................... C08L 63/00; C08L 79/08
[52] U.S. Cl. ..................................... 525/423; 528/96; 528/119; 528/322; 528/353
[58] Field of Search ................. 528/96, 117, 353, 322; 548/451; 525/423

[56] References Cited

U.S. PATENT DOCUMENTS

| | | | |
|---|---|---|---|
| 3,501,443 | 3/1970 | DiLeone | 528/352 X |
| 3,534,325 | 1/1972 | DiLeone | 528/353 X |
| 3,574,160 | 4/1971 | Hsu | 528/353 X |
| 3,607,814 | 9/1971 | DiLeone | 528/353 X |
| 3,763,114 | 10/1973 | Saluti et al. | 528/353 X |
| 4,271,079 | 6/1981 | Maeda et al. | 528/353 X |
| 4,487,894 | 12/1984 | Lee | 525/423 |

FOREIGN PATENT DOCUMENTS 62-29584 2/1987 Japan .
62-212419 9/1987 Japan .
445510 2/1968 Switzerland .
1137086 12/1968 United Kingdom .

OTHER PUBLICATIONS

Wagner-Jauregg, Chemical Abstracts, vol. 67, pp. 1067-1068, No. 11318u (1967).

Aziz et al., Chemical Abstracts, vol. 85, p. 2078, No. 20789X (1979).

Primary Examiner—Earl Nielsen

Attorney, Agent, or Firm—Wenderoth, Lind & Ponack

[57] ABSTRACT

The present invention provides an improved epoxy resin composition comprising an epoxy resin and a novel imide compound represented by the formula

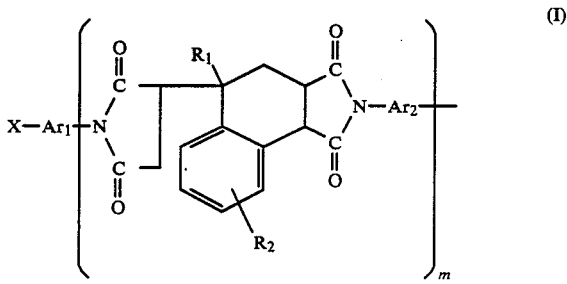

(I)

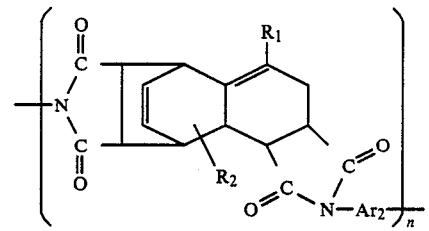

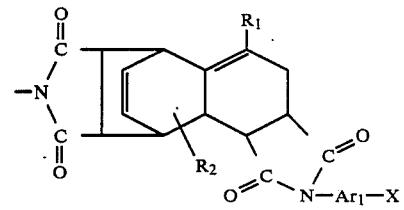

wherein X represents an $-NH_2$ group and/or $-OH$ group, $Ar_1$ and $Ar_2$ independently represent an aromatic residue, $R_1$ represents a hydrogen atom or an alkyl group having from 1 to 10 carbon atoms, $R_2$ represents a hydrogen atom, an alkyl or alkoxy group having from 1 to 20 carbon atoms or hydroxyl group, and each of m and n represents a number of from 0 to 30.

22 Claims, No Drawings

IMIDE COMPOUND AND COMPOSITION CONTAINING THE SAME

The present invention relates to a thermosettable imide compound having terminal functional groups. Also, the present invention relates to an epoxy resin composition produced with the above imide compound, and more particularly, to an epoxy resin composition suitable for lamination and molding.

Hitherto, for laminates and as encapsulant for semiconductor elements such as IC, LSI, etc. used in apparatus for industry and people's livelihood, epoxy resins have been used.

However, the cured product of epoxy resins is low in thermal resistance, and this low thermal resistance causes the laminates to produce a large change of dimension in the direction perpendicular to the substrate, so that there were problems such as lowering in through-hole reliability, smear, etc. With the encapsulant for IC, LSI, etc., there was also a problem that when parts such as IC, LSI, etc. are connected to circuits by soldering, cracks are formed by the heat of the solder because of the large thermal expansion of the material. For these reasons, improvement in the thermal resistance of the cured product has been desired.

For improving the thermal resistance of such hardened products, a method to use aromatic imide compounds as a hardener may be thought of.

Generally, aromatic imide compounds are produced with aromatic tetracarboxylic acid anhydrides and aromatic diamines as materials. The well-known representative aromatic tetracarboxylic acid anhydrides include pyromellitic acid anhydride and benzophenonetetracarboxylic acid anhydride. The aromatic imide compounds obtained with these acid anhydrides, however, are poor in compatibility with epoxy resins, so that it was difficult to use the aromatic imide compounds as a hardener for epoxy resins, thereby improving the performance of the hardened product. Also, these aromatic imide compounds are very low in solubility in the common low-boiling organic solvents, and for dissolving the imide compounds in organic solvents, special high-boiling solvents such as dimethylformamide, dimethylacetamide, N-methylpyrrolidone, dimethyl sulfoxide, cresol, etc. are necessary. Consequently, it was also difficult in this respect to use the imide compounds together with epoxy resins.

In view of the above, the present inventors have made an extensive study about an imide compound excellent in solubility and compatibility, and as a result, have found that an imide compound having a structural unit represented by the general formulae,

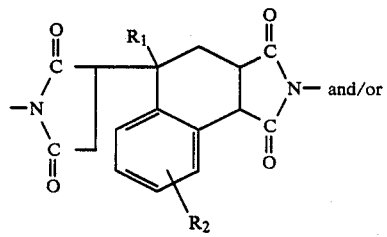 and/or

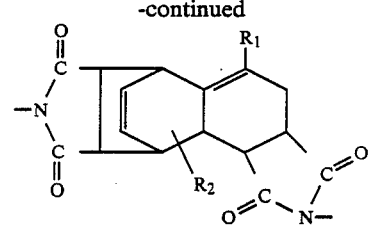

wherein $R_1$ represents a hydrogen atom or an alkyl group having from 1 to 10 carbon atoms, and $R_2$ represents a hydrogen atom, an alkyl or alkoxy group having from 1 to 20 carbon atoms or a hydroxyl group, in the molecule is easily soluble in various organic solvents and excellent in compatibility with epoxy resins, and also that, by combined use of said imide compound and epoxy resins, the foregoing problems such as low thermal resistance, large change of dimension and cracking by the action of heat can be solved. The present inventors thus arrived at to the present invention.

Further, the present inventors have found that the conventional thermosetting polyimide resins have problems in terms of adhesion to metallic surface, water resistance, etc., but that a resin composition comprising the above imide compound and epoxy resins has performances equivalent to or higher than those of epoxy resins in terms of the adhesion property and water resistance.

Thus, the present invention provides a thermosettable imide compound represented by the general formula (I),

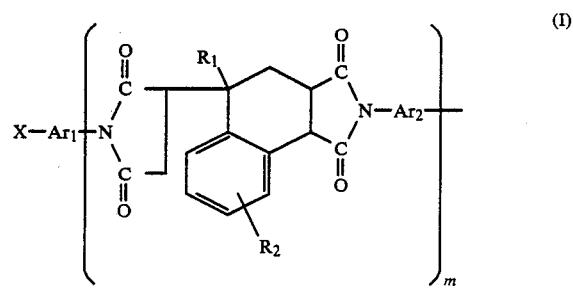 (I)

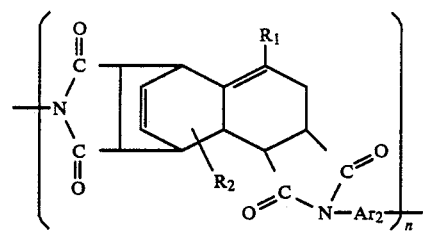

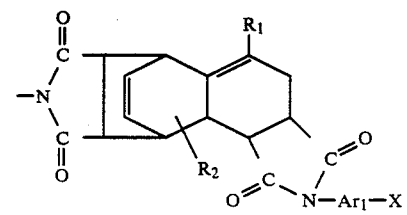

wherein X represents an —NH$_2$ group and/or —OH group, Ar$_1$ and Ar$_2$ independently represent an aromatic residue, $R_1$ represents a hydrogen atom or an alkyl group having from 1 to 10 carbon atoms, $R_2$ represents a hydrogen atom, an alkyl or alkoxy group having from 1 to 20 carbon atoms or a hydroxyl group, and each of m and n represents a number of from 0 to 30.

Also, the present invention provides an epoxy resin composition containing as essential components an epoxy resin (A) and an imide compound (B) represented by the foregoing general formula (I). The hardened product of said epoxy resin composition has excellent thermal resistance which has so far never been obtained.

Further, the present invention provides an epoxy resin composition comprising an epoxy resin (A), an imide compound (B) represented by the foregoing general formula (I) and a polymaleimide compound (C) having two or more maleimide groups in the molecule.

Further, the present invention provides an epoxy resin composition containing as essential components an epoxy resin (A), an imide compound (B) represented by the foregoing general formula (I) and a compound (D) having two or more phenolic —OH groups in the molecule (hereinafter referred to as polyphenol compound).

Further, the present invention provides an adhesive composition containing as essential components an epoxy resin (A) and an imide compound (B) represented by the foregoing general formula (1).

Referring to $Ar_1$ and $Ar_2$ in the general formula (I) in more detail, they are independently a mononuclear or polynuclear divalent aromatic residue of which the aromatic ring may or may not be substituted with a lower alkyl group, a halogen atom, a lower alkoxy group, etc. More specifically, each of $Ar_1$ and $Ar_2$ is an aromatic amine residue, $Ar_2$ being an aromatic diamine residue, and $Ar_1$ being an aromatic monoamine or diamine residue. Of these aromatic amines, the aromatic diamine includes : 4,4'-diaminodiphenylmethane, 3,3'diaminodiphenylmethane, 4,4'-diaminodiphenyl ether, 3,4'-diaminodiphenyl ether, 4,4'-diaminodiphenylpropane, 4,4'-diaminodiphenyl sulfone, 3,3'-diaminodiphenyl sulfone, 2,4-tolylenediamine, 2,6-tolylenediamine m-phenylenediamine, p-phenylenediamine, benzidine, 4,4'-diaminodiphenyl sulfide, 3,3'-dichloro-4,4'-diaminodiphenyl sulfone, 3,3'-dichloro4,4'-diaminodiphenylpropane, 3,3'-dimethyl-4,4'-diaminodiphenylmethane 3,3'-dimethoxy-4,4'-diaminobiphenyl, 3,3'-dimethyl-4,4'-diaminobiphenyl 1,3-bis(4-aminophenoxy)benzene, 1,3-bis(3-aminophenoxy)benzene, 1,4bis(4-aminophenoxy)benzene, 2,2-bis(4-aminophenoxyphenyl)propane, 4,4'-bis(4-aminophenoxy)diphenyl sulfone, 4,4'-bis(3-aminophenoxy)-diphenyl sulfone, 9,9'-bis(4-aminophenyl)anthracene, 9,9'-bis(4-aminophenyl)fluorene, 3,3'-dicarboxy-4,4'-diaminodiphenylmethane, 2,4-diaminoanisole, bis(3-aminophenyl)methylphosphine oxide, 3,3'-diaminobenzophenone, o-toluidine sulfone, 4,4'-methylene-bis-o-chloroaniline, tetrachlorodiaminodiphenylmethane, m-xylylenediamine, p-xylylenediamine 4,4'-diaminostilbene, 5-amino-1-(4'-aminophenyl)-1,3,3-trimethylindan 6-amino-1-(4'-aminophenyl)-1,3,3-trimethylindane, 5-amino-6-methyl-1-(3'-amino-4'-methylphenyl)-1,3,3-trimethylindane, 7-amino-6-methyl-(1-(3'-amino-4'-methylphenyl)-1,3,3-trimethylindane, 6-amino-5-methyl-1-(4'-amino-3'-methylphenyl)-1,3,3-trimethylindane, 6-amino-7-methyl-1-(4'-amino-3'-methylphenyl)-1,3,3-trimethylindane, etc. These compounds may be used alone or in combination.

On the other hand, the aromatic monoamine includes: o-aminophenol, m-aminophenol, p-aminophenol, 6-amino-m-cresol, 4-amino-m-cresol, 2,2-(4-hydroxyphenyl-4-aminophenyl)propane, 2,2-(4-2'hydroxyphenyl-2'-methyl-4'-aminophenyl)propane, 2,2-(3-methyl-4-hydroxyphenyl-4'-aminophenyl)propane, 3-amino-1-naphthol, 8-amino-2naphthol, 5-amino-1-naphthol, 4-amino-2-methyl-1-naphthol, etc. These compounds may be used alone or in combination.

In the general formula (I), $R_1$ and $R_2$ are as defined above, and $R_1$ is particularly preferably an alkyl group having from 1 to 3 carbon atoms and $R_2$ is particularly preferably hydrogen atom and an alkyl group having from 1 to 5 carbon atoms.

In the general formula (I), m and n are defined above, and each of m and n is preferably a number of from 0 to 8 and particularly preferably a number of from 0 to 5.

A method to produce the functional group-terminated imide compound represented by the general formula (I) will be illustrated.

Those in which X in the formula (I) is —NH$_2$ may be synthesized by reacting an excess of the foregoing aromatic diamine with a compound represented by the general formulae,

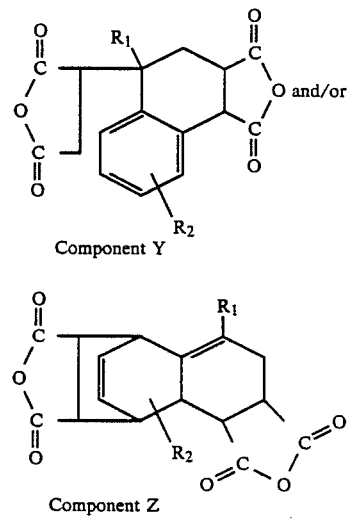

Component Y

Component Z wherein $R_1$ and $R_2$ are as defined above, (hereinafter referred to as $B_1$, and the isomers are referred to as component Y and component Z, respectively) according to the common imidation technique.

Those in which X in the formula (I) is —OH may be synthesized by adding the foregoing aromatic monoamine having an —OH group and aromatic diamine to $B_1$ so that the molar ratio of the aromatic diamine to $B_1$ is (m+n) to (m+n+1), and besides the molar ratio of the aromatic monoamine to $B_1$ is 2 to (m+n+1) (wherein m and n are as defined above), and carrying out the reaction according to the common imidation technique.

A method to synthesize the functional group-terminated imide compound reprsented by the general formula (I) has been illustrated above, but the method is not of course limited thereto.

Referring here to a synthetic method for $B_1$, $B_1$ is obtained by reacting a compound represented by the general formula,

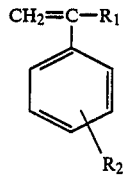

wherein R₁ and R₂ are as defined above, (hereinafter referred to as B₃) with maleic anhydride at a former to latter molar ratio of 1 to 2 in the absence of a radical polymerization catalyst and in the presence or absence of a radical polymerization inhibitor. Examples of B₃ include styrene, α-methylstyrene, α,p-dimethylstyrene, α,m-dimethylstyrene, isopropylstyrene, vinyl-toluene, p-tert-butylstyrene, p-isopropenylphenol, m-isopropenylphenol 1-methoxy-3-isopropenylbenzene, 1-methoxy-4-isopropenylbenzene, vinylxylene, etc. These compounds may be used alone or in combination.

The functional group-terminated imide compounds thus obtained are soluble in high concentrations in low-boiling solvents such as acetone, methyl ethyl ketone, methyl isobutyl ketone, methyl cellosolve, ethyl cellosolve, methylene chloride, chloroform, etc., and also they are superior in compatibility with epoxy resins. Consequently, thermo-setting is possible by combining the imide compounds and epoxy resins.

The epoxy resin (A) used in the composition or adhesive of the present invention is a compound having two or more epoxy groups in the molecule. Examples of the epoxy resin include glycidyl ether compounds derived from dihydric or more phenols [e.g. bisphenol A, bisphenol F, hydroquinone, resorcinol, phloroglucinol, tris(4-hydroxyphenyl)methane, 1,1,2,2-tetrakis(4-hydroxyphenyl)ethane] or halogenated polyphenols (e.g. tetrabromobisphenol A, brominated phenol novolak); novolak type epoxy resins derived from novolak resins which are reaction products of phenols (e.g. phenol, o-cresol) with formaldehyde; amine type epoxy resins derived from aniline, p-aminophenol, m-aminophenol, 4-amino-m-cresol, 6-amino-m-cresol, 4,4'-diaminodiphenylmethane, 3,3'-diaminodiphenylmethane, 4,4'-diaminodiphenyl ether, 3,4'-diaminodiphenyl ether, 1,4-bis(4-aminophenoxy)benzene, 1,4-bis(3-aminophenoxy)benzene, 1,3-bis(4-aminophenoxy)benzene, 1,3-bis(3-aminophenoxy)benzene, 2,2-bis(4-aminophenoxyphenyl)propane, p-phenylenediamine, m-phenylenediamine, 2,4-tolylenediamine, 2,6-tolyenediamine, p-xylylenediamine, m-xylylenediamine, 1,4-cyclohexane-bis(methylamine), 1,3-cyclohexane-bis(-methylamine), 5-amino-1-(4'-aminophenyl)-1,3,3-trimethylindane, 6-amino-1-(4'-aminophenyl)-1,3,3-trimethylindane, etc.; glycidyl ester compounds derived from aromatic carboxylic acids (e.g. p-oxybenzoic acid, m-oxybenzoic acid, terephthalic acid, isophthalic acid); hydantoin type epoxy resins derived from 5,5-dimethylhydantoin, etc.; alicyclic epoxy resins such as 2,2'-bis(3,4-epoxycyclohexyl)propane, 2,2-bis[4-(2,3epoxypropyl)cyclohexyl]propane, vinylcyclohexene dioxide, 3,4-epoxycyclohexylmethyl-3,4-epoxycyclohexanecarboxylate, etc.; and other compounds such as triglycidyl isocyanulate, 2,4,6-triglycidoxy-S-triazine, etc. These epoxy resins may be used alone or in combination.

As to the proportion of the epoxy resin (A) and the functional group-terminated imide compound (B), it is preferred that the sum of (B) and a hardener described later is from 0.6 to 1.2 gram equivalent per 1 gram equivalent of (A).

In order to attain further improvement in the thermal resistance of the foregoing epoxy resin composition comprising the epoxy resin (A) and imide compound (B), a compound having two or more maleimide groups represented by the general formula (II),

wherein R₃ represents a hydrogen atom or a lower alkyl group, in the molecule, i.e. a polymaleimide compound (C) may be incorporated in said composition.

Specific examples of the polymaleimide compound (C) includes N,N'-bismaleimide compounds such as N,N'-diphenylmethane bismaleimide, N,N'-phenylene bismaleimide, N,N'-diphenylether bismaleimide, N,N'diphenylsulfone bismaleimide, N,N'-dicyclohexylmethane bismaleimide, N,N'-tolylene bismaleimide, N,N'-xylylene bismaleimide, N,N'-diphenylcyclohexane bismaleimide, N,N'-dichlorodiphenylmethane bismaleimide, N,N'-diphenylcyclohexane bismaleimide, N,N'-diphenylmethane bis (methylmaleimide), N,N'-diphenylether bis(methylmaleimide), N,N'diphenylsulfone bis(methylmaleimide), isomers of these compounds, N,N'-ethylene bismaleimide, N,N'-hexamethylene bismaleimide, N,N'hexamethylene bis(methylmaleimide); prepolymers having an N,N'bismaleimide skeleton at the terminal obtained by the addition of these N,N'-bismaleimide compounds and diamines; and the maleimidated or methylmaleimidated compounds of aniline.formalin polycondensation products.

Particularly, N,N'-diphenylmethane bismaleimide and N,N'-diphenylether bismaleimide are preferred.

As to the proportion of the components of the resin composition of the present invention comprising the epoxy resin (A), imide compound (B) and polymaleimide compound (C), it is generally preferred that the proportion of the epoxy resin (A) and imide compound (B) is from 0.6 to 1.2 gram equivalent of (B) per 1 gram equivalent of (A), that of the polymaleimide compound (C) and imide compound (B) is from 0.6 to 1, as the number of active hydrogen atoms H in the terminal functional group of (B), per 1 double bond in (C), and that the weight ratio of (A) and (C), i.e. (A)/(C), is from 95/5 to 40/60. However, when other epoxy hardeners described later are used, it is preferred that the proportion of the epoxy resin (A) and functional group-terminated imide compound (B) is from 0.6 to 1.2 gram equivalent as the sum of (B) and the hardeners, per 1 gram equivalent of (A).

Into the foregoing composition comprising the epoxy resin (A) and imide compound (B) and composition comprising the epoxy resin (A), imide compound (B) and polymaleimide compound (C) may be incorporated a polyphenol compound (D) having two or more phenolic —OH groups in the molecule in order to improve the hardening property and hardening rate of the compositions.

Examples of such polyphenol compound includes dihydric or more phenols [e.g. bisphenol A, bisphenol F, hydroquinone, resorcinol, phloroglucinol, tris(4-hydroxyphenyl)methane, 1,1,2,2-tetrakis(4hydroxyphenyl)ethane]; halogenated bisphenols (e.g. tetrabromobisphenol A); and novolak type condensation products which are a reaction product of a phenol [e.g. phenol, cresols (including isomers), xylenols (including isomers), hydroquinone, resorcinol, p-tert-butylphenol, p-tert-octylphenol, allylphenols (including isomers), bisphenol A, vinylphenol, etc.] and formaldehyde.

As to the proportion of the components of the resin composition of the present invention comprising the epoxy resin (A), imide compound (B) and polyphenol compound (D), it is generally preferred that the ratio of the number of active hydrogen atoms in the terminal functional group X of (B) to the number of —OH groups in (D), i.e. (B)/(D), is from 2/1 to 4/1, and besides the sum of the active hydrogen equivalents of (B) and (D) is from 0.6 to 1.2 gram equivalent per 1 gram equivalent of (A).

However, when other epoxy hardeners described later are used, it is preferred that the sum of (B), (D) and the hardeners is selected so as to be from 0.6 to 1.2 gram equivalent per 1 gram equivalent of (A).

As to the proportion of the components of the resin composition comprising the epoxy resin (A), imide compound (B), polymaleimide compound (C) and polyphenol compound (D), it is generally preferred that the sum of the active hydrogen equivalent of (B) and that of (D) is from 0.6 to 1.2 gram equivalent per 1 gram equivalent of (A), and the ratio of the active hydrogen equivalent of (B) to that of (D), i.e. (8)/(D), is from 2/1 to 4/1.

However, when other epoxy hardeners described later are used, it is preferred that the sum of (B), (D) and the hardeners is selected so as to be from 0.6 to 1.2 gram equivalent per 1 gram equivalent of (A).

It is preferred to select the polymaleimide compound (D) so as to be from 2.5 to 30% of the total weight.

The epoxy resin composition of the present invention contains the epoxy resin (A), functional group-terminated imide compound (B) and if necessary the polymaleimide compound (C) and/or polyphenol compound (D), all of which are explained above, but said epoxy resin composition may contain, in addition to these components, the known epoxy hardeners and cure accelerators, fillers, flame retardants, reinforcing agents, surface-treating agents, pigments, etc. as need arises.

The well-known epoxy hardeners include amine type hardeners such as aromatic amines (e.g. xylylenediamine) and aliphatic amines, acid anhydrides, dicyandiamide, hydrazide compounds, etc.

The cure accelerators include amines [e.g. benzyldimethylamine, 2,4,6-tris(dimethylaminomethyl)phenol, 1,8-diazabicycloundecene] imidazole compounds (e.g. 2-ethyl-4-methylimidazole), boron trifluoride amine complexes, etc. The fillers include silica, calcium carbonate, etc.; the flame retardants include aluminum hydroxide, antimony trioxide, red phosphorus, etc.; and the reinforcing agents include fabrics comprising glass fibers or organic fibers (e.g. polyester fibers, polyamide fibers), alumina fibers, non-woven fabrics mats, papers and combination thereof.

The epoxy resin composition according to the present invention gives hardened products having an extremely high thermal resistance that has so far never been obtained, and therefore, it is of industrially very high value as a material for lamination and molding. Also, it is excellent in adhesion to metallic surface and water resistance.

For example, epoxy resin copper-clad laminates produced with the epoxy resin composition of the present invention have a very high thermal resistance that could so far never be obtained, and besides they are excellent in adhesion to copper foil and water resistance. The epoxy resin copper-clad laminates referred to herein are obtained by impregnating a substrate for laminate with an organic solvent solution of the epoxy resin composition of the present invention, removing the solvent by drying to prepare a prepreg and heat-laminating the prepreg and copper foil. The substrate for laminate includes fabrics comprising inorganic fibers (e.g. glass fibers) or organic fibers (e.g. polyester fibers, polyamide fibers), non-woven fabrics, mats, papers and combinations thereof. The organic solvent includes acetone, methyl ethyl ketone, methyl isobutyl ketone, methyl cellosolve ethyl cellosolve, dimethylformamide, etc. For the heat-molding condition, there is given press molding carried out at a temperature of from 150° to 250° C. under a pressure of from 10 to 100 kg/cm$^2$ for from 20 to 300 minutes.

Also, the composition comprising the epoxy resin (A), imide compound (B) and polymaleimide compound (C) has particularly a high thermal resistance.

Further, the composition comprising the epoxy resin (A), imide compound (B) and polyphenol compound (D) has a high hardening rate, and is of a very high industrial value.

As described above, the composition of the present invention comprising the epoxy resin (A) and imide compound (B) gives hardened products having a high thermal resistance and adhesion property which have so far never been obtained, is used as an adhesive and of a high industrial value. When the composition is used as an industrial adhesive, it is kneaded on a roll at a temperature of from 110° to 50° C. to prepare a uniform mixture which is then formed into sheet, and the sheet is used as the adhesive. Also, the composition may be used in such a manner that it is dissolved in a solvent such as dimethylformamide, methyl cellosolve, acetone, etc. and the resulting solution is directly coated onto adherends. Further, the composition may also be used in such a manner that the solution obtained above is impregnated into a reinforcing material such as glass fibers and the material is dried at a temperature of from 150° to 180° C. for from 5 to 10 minutes to prepare a prepreg which is then used as the adhesive.

The imide compound (B) of the present invention has been illustrated with reference to the compositions produced by combining (B) and the epoxy resin (A). The imide compound, however, can also be used in systems containing no epoxy resins. In this case, the fillers, flame retardants, reinforcing agents, surface-treating agents pigments, etc. described above can also be used together as need arises.

The composition of the present invention comprising the imide compound (B) and polymaleimide compound (C) is a thermosetting resin composition which needs no high-temperature prolonged heating at the time of molding, and which is superior in moldability as well as thermal resistance and mechanical and electrical characteristics at high temperatures and useful as a material for lamination and mold. Consequently, the composition of the present invention is of a high industrial value.

As to the proportion of the components of this resin composition, it is preferred that the number of active hydrogen atoms H in the terminal functional group X of the imide compound (B) is in a range of from 0.6 to 1.0 per 1 double bond in the polymaleimide compound (C).

This resin composition can also be used together with fillers, flame retardants, reinforcing agents, surface-treating agents pigments, etc. as need arises.

The present invention will be illustrated in more detail with reference to the following examples.

Synthetic example 1

Synthesis of material $B_1$

To a 500-ml four-necked flask equipped with a stirrer, thermometer and condenser, were charged 110.3 g (1.125 moles) of maleic anhydride, 3.90 g of N,N'-diphenyl-1,4-phenylenediamine, 100 g of toluene and 50 g of methyl isobutyl ketone. Subsequently, the temperature was raised to 120° C., and 59.1 g (0.5 mole) of α-methylstyrene was added dropwise over 8 hours while keeping the same temperature, after which the same temperature was kept for a further 2 hours. After reaction, on cooling the reaction solution with addition of 50 g of toluene and 25 g of methyl isobutyl ketone, crystals precipitated. The crystals were filtered off, washed with toluene several times and dried to obtain 55.7 g of nearly white powdery crystals.

The purity of $B_1$ of this crystal by means of GPC was 97.2%, the composition of $B_1$ isomers by means of GC was 0.45/0.55 in terms of Y component/Z component, and the melting point of this crystal was 206°–208° C.

Synthetic example 2

To a 500-ml four-necked flask equipped with a stirrer, thermometer and condenser were charged 98.1 g (1 mole) of maleic anhydride, 3.90 g of N,N'-diphenyl-1,4-phenylenediamine and 150 g of xylene. Subsequently, the temperature was raised to 145° C., and 59.1 g (0.5 mole) of α-methylstyrene was added dropwise over 8 hours while keeping the same temperature, after which the same temperature was kept for further 2 hours. After reaction, on cooling the reaction solution with addition of 75 g of methyl isobutyl ketone, crystals precipitated. The crystals were filtered off, washed with toluene several times and dried to obtain 50.4 g of nearly white powdery crystals.

The purity of $B_1$ of this crystal by means of GPC was 96.1%, the composition of $B_1$ isomers by means of GC was 0.17/0.83 in terms of Y component/Z component, and the melting point of this crystal was 208°–210° C.

Synthetic example 3

To a 500-ml four-necked flask equipped with a stirrer, thermometer and condenser, were charged 98.1 g (1 mole) of maleic anhydride, 4.51 g of N-phenyl-N'-isopropyl-1,4-phenylenediamine, 120 g of toluene and 30 g of methyl isobutyl ketone. Subsequently the temperature was raised to 120° C., and 59.1 g (0.5 mole) of α-methylstyrene was added dropwise over 2 hours while keeping the same temperature, after which the same temperature was kept for a further 8 hours. After reaction, on cooling the reaction solution with addition of 60 g of toluene and 15 g of methyl isobutyl ketone, crystals precipitated. The crystals were filtered off, washed with toluene several times and dried to obtain 67.2 g of nearly white powdery crystals.

The purity of $B_1$ of this crystal by means of GPC was 97.8%, the composition of $B_1$ isomers by means of GC was 0.66/0.34 in terms of Y component/Z component, and the melting point of this crystal was 181°–183° C.

EXAMPLE 1

To a flask equipped with a stirrer, thermometer and separator, were charged 26.2 g (0.215 mole) of 2,4-tolylenediamine and 117 g of m-cresol, and after raising the temperature to 70° C. to dissolve,2,4-tolylenediamine, 45.0 g (0.143 mole) of the material obtained in Synthetic example 1 was added to form a polyamide acid. Thereafter 25.2 g of toluene was added, and after raising the temperature to 150° C., dehydration was continued for 10 hours at the same temperature.

After reaction, the resulting resin solution was added to 750 g of isopropanol to form precipitates which were then washed twice and dried under reduced pressure to obtain an imide compound. The amine equivalent of this compound was 498 g/eq, and the melting point thereof was about 260° C.

EXAMPLE 2

To a flask equipped with a stirrer, thermometer and separator were charged 44.8 g (0.143 mole) of the material obtained in Synthetic example 1, 161 g of m-cresol and 8.68 g (0.0714 mole) of 2,4-tolylenediamine, and reaction was carried out at a temperature of 70° C. for 1 hour. Subsequently, 15.5 g (0.143 mole) of m-aminophenol was added, and reaction was carried out at the same temperature for 1 hour. Thereafter, 32.2 g of xylene was added, and dehydration was continued at a temperature of 170° C. for 6 hours.

After reaction, the resulting resin solution was added to 550 g of isopropanol to form precipitates which were then washed twice and dried under reduced pressure to obtain an imide compound. The hydroxyl equivalent of this compound was 473 g/eq, and the melting point thereof was 270° C.

EXAMPLE 3

An imide compound was obtained under the same condition as in Example 1 except that 26.2 g (0.215 mole) of 2,4-tolylenediamine was replaced by 19.3 g (0.0971 mole) of 4,4'-diaminodiphenylmethane, and 45.0 g (0.143 mole) of the material obtained in Synthetic example 1 was replaced by 26.7 g (0.085 mole) of the material obtained in Synthetic example 2. The amine equivalent of this compound was 1690 g/eq, and the melting point thereof was not less than 300° C.

EXAMPLE 4

An imide compound was obtained under the same condition as in Example 2 except that 44.8 g (0.143 mole) of the material obtained in Synthetic example 1 was replaced by 32.0 g (0.102 mole) of the material obtained in Synthetic example 2, 8.68 g (0.0714 mole) of 2,4-tolylenediamine was replaced by 12.9 g (0.0639 mole) of 4,4'-diaminodiphenylmethane, and that the amount of m-aminophenol was changed to 8.30 g (0.0761 mole). The hydroxyl equivalent of this compound was 702 g/eq, and the melting point thereof was about 270° C.

EXAMPLE 5

An imide compound was obtained under the same condition as in Example 1 except that the material obtained in Synthetic example 1 was replaced by the material obtained in Synthetic example 3. The amine equivalent of this compound was 506 g/eq, and the melting point thereof was about 260° C.

EXAMPLE 6

An imide compound was obtained under the same condition as in Example 2 except that the material obtained in Synthetic example 1 was replaced by the material obtained in Synthetic example 3. The hydroxyl equivalent of this compound was 478 g/eq, and the melting point thereof was about 260° C.

The imide compounds obtained in Examples 1 to 6 are soluble in solvents such as acetone, MEK, methylene chloride, methyl cellosolve, etc., and also their compatibility with epoxy resins is good.

EXAMPLE 7

An imide compound was obtained under the same condition as in Example 1 except that 26.2 g (0.215 mole) of 2,4-tolylenediamine was replaced by 11.9 g (0.0971 mole) of 2,4'-tolylenediamine and 45.0 g (0.143 mole) of the material obtained in Synthetic example 1 was replaced by 26.7 g (0.085 mole) of the material obtained in Synthetic example 3. The amine equivalent of this compound was 1480 g/eq, and the melting point thereof was not less than 300° C.

EXAMPLES 8 and 9

Sumi® epoxy ELA-128 (bisphenol A type epoxy resin having an epoxy equivalent of 187 g/eq; product of Sumitomo Chemical Co., Ltd.) and each of the imide compounds obtained in Examples 1 and 5 were blended in a proportion shown in Table 1. The resulting blends were each uniformly dissolved in dimethylformamide and impregnated into glass cloth (WE18K, BZ-2; products of Nitto boseki K.K.) which was then treated for 5 minutes in a 180° C. oven to obtain a prepreg. Six pieces of this prepreg and copper foil (TAI-treated foil of 35μ in thickness; product of Furukawa Circuit Foil Co., Ltd.) were piled up and press-molded, at a temperature of 180° C. for 5 hours under a pressure of 50 kg/cm², into a copper-clad laminate of 1 mm in thickness. The physical properties of this laminate were measured according to JIS-C-6481 to obtain the results shown in Table 1.

COMPARATIVE EXAMPLE 1

240 Grams of Sumi® epoxy ESA-011 (bisphenol A type epoxy resin having an epoxy equivalent of 489 g/eq; product of Sumitomo Chemical Co., Ltd.), 20 g of Sumi® epoxy ESCN-220 (o-cresol novolak type epoxy resin having an epoxy equivalent of 210 g/eq; product of Sumitomo Chemical Co., Ltd.), 9 g of dicyandiamide and 1 g of 2-phenyl-4-methyl-5-hydroxymethylimidazole were dissolved in a mixed solvent comprising 40 g of dimethylformamide, 60 g of ethylene glycol monomethyl ether and 60 g of methyl ethyl ketone. In the same manner as in Example 8, this solution was impregnated into glass cloth, and the glass cloth was treated for 5 minutes in a 160° C. oven to obtain a prepreg which was then press-molded into a laminate. The physical properties of this laminate are shown in Table 1.

TABLE 1

| Example | | Example 8 | Example 9 | Comparative example 1 |
|---|---|---|---|---|
| Sumi® epoxy ELA-128 (g) | | 100 | 100 | |
| Imide compound in Example 1 (g) | | 133 | — | |
| Imide compound in Example 5 (g) | | — | 135 | |
| $T_g$ | °C. | 198 | 201 | 124 |
| Expansion coefficient of Z axis (not higher than $T_g$) | 1/°C. | $3.5 \times 10^{-5}$ | $3.5 \times 10^{-5}$ | $5.7 \times 10^{-5}$ |
| Expansion coefficient of Z axis (20°–200° C.) | % | 1.06 | 1.09 | 3.15 |
| Expansion coefficient of Z axis (20°–260° C.) | % | 2.38 | 2.22 | 4.63 |
| Water absorption (after 24 hours' boiling) | % | 1.34 | 1.29 | 1.94 |
| Water absorption (after 48 hours' boiling) | % | 1.47 | 1.44 | 2.18 |
| Peeling strength of copper foil | kg/m | 228 | 239 | 210 |
| Solder resistance (300° C.) | Appearance | Pass | Pass | Blister |
| Gelation time (170° C.) | % | 16 | 15 | — |

EXAMPLES 10 and 11

100 Grams of Sumi® epoxy ESCN-195XL (o-cresol novolak type epoxy resin having an epoxy equivalent of 197 g/eq; product of Sumitomo Chemical Co., Ltd.), 25 g of each of the imide compounds obtained in Examples 2 and 4, 51 g of a phenol novolak resin, 1 g of 2,4,6-tris(-dimethylaminomethyl)phenol, 1 g of carnauba wax, 2 g of a silane coupling agent (Toray Silicone SH-6040) and 420 g of silica were kneaded on a two-roll mill for 5 minutes, cooled and pulverized to obtain a molding material. This molding material was press-molded at a temperature of 170° C. for 5 minutes under pressure of 70 kg/cm². On placing the press-molded product in a 180° C. oven, it hardened after 5 hours. The physical properties of the cured product are shown in Table 2.

COMPARATIVE EXAMPLE 2

A hardened product was obtained in the same manner as in Example 10 except that 56 g of the phenol novolak resin only was used as a hardener and 364 g of silica was used as a filler.

The physical properties of the cured product are collectively shown in Table 2.

TABLE 2

| Example | | Example 10 | Example 11 | Comparative example 2 |
|---|---|---|---|---|
| $T_g$ | °C. | 192 | 194 | 170 |
| Expansion coefficient ($<T_g$) | 1/°C. | $2.0 \times 10^{-5}$ | $2.0 \times 10^{-5}$ | $2.6 \times 10^{-5}$ |
| Expansion coefficient | % | 1.12 | 1.20 | 1.35 |

TABLE 2-continued

| Example | | Example 10 | Example 11 | Comparative example 2 |
|---|---|---|---|---|
| (20°-260° C.) | | | | |
| Flexural strength (20° C.) | kg/mm² | 14.9 | 14.7 | 14.8 |
| Flexural strength (100° C.) | " | 14.0 | 13.6 | 12.1 |
| Flexural strength (150° C.) | " | 12.9 | 12.1 | 9.0 |
| Flexural strength (180° C.) | " | 8.8 | 7.4 | 2.1 |

EXAMPLES 12, 13 and 14

Sumi® epoxy ELA-128 (bisphenol A type epoxy resin having an epoxy equivalent of 186 g/eq; product of Sumitomo Chemical Co., Ltd.), the imide compound obtained in Example 1 and N,N'-diphenylmethane bismaleimide (hereinafter referred to as BMI; product of Sumitomo Chemical Co., Ltd.) were blended in a proportion shown in Table 3. The resulting blend was uniformly dissolved in dimethylformamide and impregnated into glass cloth (WE18K, BZ-2; products of Nitto Boseki K.K.) which was then treated for 5 minutes in a 180° C. oven to obtain a prepreg. Six pieces of this prepreg and copper foil (TAI-treated foil of 35μ in thickness; product of Furukawa Circuit Foil Co., Ltd.) were piled up and press-molded, at a temperature of 200° C. for 5 hours under a pressure of 50 kg/cm², into a copper-clad laminate of 1 mm in thickness. The physical properties of this laminate were measured according to JIS-C-6481 to obtain the results shown in Table 3.

EXAMPLES 15 to 19

Sumi® epoxy ELA-128 (bisphenol A type epoxy resin having an epoxy equivalent of 186 g/eq; product of Sumitomo Chemical Co., Ltd.), Sumi® epoxy ESB-400 (brominated bisphenol A type epoxy resin having an epoxy equivalent of 400 g/eq; product of Sumitomo Chemical Co., Ltd.), the imide compound obtained in Example 1 and each of o-cresol novolak resin (softening point, 105° C.) and bisphenol A were blended in a proportion shown in Table 4. The resulting blends were each uniformly dissolved in dimethylformamide and impregnated into glass cloth (WE18K, BZ-2; products of Nitto Boseki K.K.) which was then treated for 5 minutes in a 180° C. oven to obtain a prepreg. Six pieces of this prepreg and copper foil (TAI-treated foil of 35μ in thickness; product of Furukawa Circuit Foil Co., Ltd.) were piled up and press-molded, at a temperature of 180° C. for 5 hours under a pressure of 50 kg/cm², into a copper-clad laminate of 1 mm in thickness The physical properties of this laminate were measured according to JIS-C-6481 to obtain the results shown in Table 4.

TABLE 3

| Example | | Example 12 | Example 13 | Example 14 | Comparative example 1 |
|---|---|---|---|---|---|
| Sumi® epoxy ELA-128 (g) | | 100 | 100 | 100 | — |
| Imide compound in Example 1 (g) | | 166 | 205 | 275 | — |
| BMI (g) | | 33 | 66 | 125 | — |
| $T_g$ | °C. | 267 | 276 | 273 | 124 |
| Peeling strength of copper foil | kg/m | 205 | 195 | 171 | 210 |
| Water absorption (after 24 hours' boiling) | % | 1.26 | 1.35 | 1.37 | 1.94 |
| Water absorption (after 48 hours' boiling) | % | 1.34 | 1.42 | 1.43 | 2.18 |
| Solder resistance (300° C.) Normal state | Appearance | Pass | Pass | Pass | Blister |
| After 2 hours' boiling | Appearance | Pass | Pass | Pass | Blister |

TABLE 4

| Example | | Example 15 | Example 16 | Example 17 | Example 18 | Example 19 | Comparative example 1 |
|---|---|---|---|---|---|---|---|
| Sumi® epoxy ELA-128 (g) | | 55 | 55 | 55 | 55 | 55 | |
| Sumi® epoxy ESB-400 (g) | | 45 | 45 | 45 | 45 | 45 | |
| Imide compound in Example 1 (g) | | 64.2 | 72.2 | 64.2 | 64.1 | 72.2 | |
| o-Cresol novolak resin (g) | | 15.3 | 11.5 | 10.2 | 7.7 | — | |
| Bisphenol A (g) | | — | — | — | — | 9.4 | |
| Peeling strength of copper foil | kg/m | 195 | 205 | 212 | 215 | 203 | 210 |
| Water absorption (after 24 hours' boiling) | % | 1.15 | 1.20 | 1.10 | 1.20 | 1.17 | 1.94 |
| Water absorption (after 48 hours' boiling) | % | 1.27 | 1.27 | 1.17 | 1.29 | 1.25 | 2.18 |
| Solder resistance (300° C.) Normal state | Appearance | Pass | Pass | Pass | Pass | Pass | Blister |
| After 2 hours' boiling | Appearance | Pass | Pass | Pass | Pass | Pass | Blister |
| $T_g$ | °C. | 210 | 215 | 210 | 220 | 215 | 124 |

TABLE 4-continued

| Example | | Example 15 | Example 16 | Example 17 | Example 18 | Example 19 | Comparative example 1 |
|---|---|---|---|---|---|---|---|
| Gelation time (170° C.) | min. | 6 | 7.5 | 8 | 10 | 8 | — |

EXAMPLES 20 and 21

Sumi® epoxy ELA-128 (bisphenol A type epoxy resin having an epoxy equivalent of 186 g/eq; product of Sumitomo Chemical Co., Ltd.), Sumi® epoxy ESB-400 (brominated bisphenol A type epoxy resin having an epoxy equivalent of 400 g/eq; product of Sumitomo Chemical Co., Ltd.), the imide compound obtained in Example 1, o-cresol novolak resin (softening point, 105° C.) and N,N'-diphenylmethane bismaleimide hereinafter referred to as BMI; product of Sumitomo Chemical Co., Ltd.) were blended in a proportion shown in Table 5. The resulting blends were each uniformly dissolved in dimethylformamide and impregnated into glass cloth (WE18K, BZ-2; products of Nitto Boseki K.K.) which was then treated for 5 minutes in a 180° C. oven to obtain a prepreg. Six pieces of this prepreg and copper foil (TAI-treated foil of 35μ in thickness; product of Furukawa Circuit Foil Co. Ltd.) were piled up and press-molded, at a temperature of 180° C. for 5 hours under a pressure of 50 kg/cm², into a copper-clad laminate of 1 mm in thickness. The physical properties of this laminate were measured according to JIS-C-6481 to obtain the results shown in Table 5.

hered to each other so that the adhesion area was 15 mm × 25 mm and hardened by applying heat-treatment at a temperature of 200° C. for 2 hours under a pressure of about 3 kg/cm². Thus, five test pieces were prepared for each adhesive composition. Using these test pieces, overlap shear strength at temperatures of 20° C., 100° C., 150° C. and 200° C. was measured. The results are shown in Table 6.

COMPARATIVE EXAMPLE 3

100 Grams of Sumi® epoxy ESA-011 (bisphenol A type epoxy resin having an epoxy equivalent of 478 g/eq; product of Sumitomo Chemical Co., Ltd.), 4 g of dicyandiamide, 1.5 g of 2-ethyl-4methylimidazole and 17 g of Hycar CTBN 1300×13 (B, F; products of Goodrich Chemical Co., Ltd.), which was a nitrile rubber component, were blended. The blend was measured for overlap shear strength in the same manner as in Example 22 except that the heat-treatment was carried out under a condition of 140° C.×3 hours. The result is shown in Table 6.

COMPARATIVE EXAMPLE 4

100 Grams of Sumi® epoxy ELM-434 (glycidyla-

TABLE 5

| Example | | Example 20 | Example 21 | Comparative example 1 |
|---|---|---|---|---|
| Sumi ® epoxy ELA-128 (g) | | 55 | 55 | |
| Sumi ® epoxy ESB-400 (g) | | 45 | 45 | |
| Imide compound in Example 1 (g) | | 120 | 108 | |
| o-Cresol novolak resin (g) | | 9 | 9 | |
| BMI (g) | | 30 | 20 | |
| Peeling strength of copper foil | kg/m | 190 | 200 | 210 |
| Water absorption (after 24 hours' boiling) | % | 1.31 | 1.20 | 1.94 |
| Water absorption (after 48 hours' boiling) | % | 1.39 | 1.27 | 2.18 |
| Solder resistance (300° C.) | Normal state Appearance | Pass | Pass | Blister |
| | After 2 hours' boiling Appearance | Pass | Pass | Blister |
| $T_g$ | °C. | 250 | 256 | 124 |
| Gelation time (170° C.) | min | 3.5 | 4.5 | — |

EXAMPLES 22 and 23

Sumi® epoxy ELA-128 (bisphenol A type epoxy resin having an epoxy equivalent of 186 g/eq; product of Sumitomo Chemical Co., Ltd.) and each of the imide compounds obtained in Examples 1 and 5 were blended in a proportion shown in Table 6 and kneaded on a mixing roll at a temperature of from 110° to 50° C. for 10 minutes to obtain an adhesive composition. The adhesive compositions were each coated in a molten state onto two pieces of soft steel plate, 1.6 mm in thickness, 25 mm in width and 100 mm in length, previously surface-polished rinsed and defatted according to JIS-K-6850. Two pieces of the soft steel plate were then admine type epoxy resin having an epoxy equivalent of 120 g/eq; product of Sumitomo Chemical Co., Ltd.), which was a polyfunctional epoxy resin, 47.9 g of 4,4'-diaminodiphenylsulfone and 1 g of boron trifluoride/-monoethylamine complex were blended. The blend was measured for overlap shear strength in the same manner as in Example 22. The result is shown in Table 6.

COMPARATIVE EXAMPLE 5

Using Kelimide 601S (product of Nippon Polyimide K.K.), overlap shear strength was measured in the same manner as in Example 22 except that the heat-treatment was carried out under a condition of 200° C.×5 hours. The result is shown in Table 6.

TABLE 6

| Example | | Example 22 | Example 23 | Comparative example 3 | Comparative example 4 | Comparative example 5 |
| --- | --- | --- | --- | --- | --- | --- |
| Sumi ® epoxy ELA-128 (g) | | 100 | 100 | | | |
| Imide compound in Example 1 (g) | | 133 | — | | | |
| Imide compound in Example 5 (g) | | — | 135 | | | |
| | 20° C. | 200 | 204 | 280 | 141 | 69 |
| Overlap shear strength | 100° C. | 164 | 169 | 140 | 141 | 70 |
| (kg/cm²) | 150° C. | 155 | 157 | 30 | 140 | 61 |
| | 200° C. | 144 | 148 | 17 | 132 | 60 |

EXAMPLES 24 and 25

Sumi ® an epoxy ELA-128 (bisphenol A type epoxy resin having equivalent of 186 g/eq; product of Sumitomo Chemical Co., Ltd.) and each of the imide compounds obtained in Examples 2 and 4 were blended in a proportion shown in Table 7 and kneaded on a mixing roll at a temperature of from 110° to 50° C. for 10 minutes to obtain an adhesive composition. Sixty grams of each composition was dissolved in 40 g of dimethylformamide and impregnated into glass cloth (WE116, EBY52; products of Nitto Boseki K.K.) which was then treated for 5 minutes in a 180° C. oven to prepare a prepreg.

This prepreg was cut into a size of 25 mm (width)×180 mm length), put between two pieces of aluminum alloy (JIS-A-2017), 25 mm (width)×200 mm (length)×0.5 mm (thickness), previously surface-polished, rinsed and defatted, and adhered and hardened by applying heat-treatment at a temperature of 200° C. for 2 hours under a pressure of 15 kg/cm². Thus, five test pieces were prepared for each adhesive composition. Using these test pieces, peeling strength was measured at temperatures of 20° C., 100° C., 150° C. and 200° C. according to JIS-K-6854. The results are shown in Table 7.

COMPARATIVE EXAMPLE 6

In the same manner as in Example 24, a varnish, prepared by dissolving 60 g of the adhesive composition obtained in Comparative example 3 in 40 g of methyl cellosolve, was impregnated into glass cloth which was then treated at a temperature of 150° C. for 5 minutes to prepare a prepreg. Thereafter, peeling strength was measured in the same manner as in Example 24 except that the heat-treatment was carried out at a temperature of 140° C. for 3 hours. The result is shown in Table 7.

COMPARATIVE EXAMPLE 7

Sixty grams of the adhesive composition obtained in Comparative example 4 was dissolved in 40 g of dimethylformamide, and treatment after that was carried out in the same manner as in Example 24 to measure peeling strength. The result is shown in Table 7.

COMPARATIVE EXAMPLE 8

Sixty grams of Kelimide 601S was dissolved in 40 g of dimethylformamide, and treatment after that was carried out in the same manner as in Example 24 except that the heat-treatment was carried out at a temperature of 200° C. for 5 hours, to measure peeling strength. The result is shown in Table 7.

It is apparent from Tables 6 and 7 that the adhesive compositions of the present invention have excellent thermal resistance and adhesion property.

TABLE 7

| Example | | Example 24 | Example 25 | Comparative example 6 | Comparative example 7 | Comparative example 8 |
| --- | --- | --- | --- | --- | --- | --- |
| Sumi ® epoxy ELA-128 (g) | | 100 | 100 | | | |
| Imide compound in Example 2 (g) | | 228 | — | | | |
| Imide compound in Example 4 (g) | | — | 337 | | | |
| | 20° C. | 3.4 | 3.5 | 5.1 | 0.32 | 0.53 |
| peeling strength | 100° C. | 3.4 | 3.5 | 4.6 | 0.23 | 0.36 |
| (kg/cm) | 150° C. | 3.5 | 3.5 | 1.4 | 0.19 | 0.25 |
| | 200° C. | 3.1 | 3.2 | 0.6 | 0.16 | 0.27 |

EXAMPLES 26, 27 and 28

N,N'-diphenylmethane bismaleimide (BMI; product of Sumitomo Chemical Co., Ltd.), the imide compound obtained in Example 1 and Sumi ® epoxy ELA-128 (bisphenol A type epoxy resin having an epoxy equivalent of 186 g/eq; product of Sumitomo Chemical Co., Ltd.) were blended in a proportion shown in Table 8. The resulting blend was mixed with heating and press-molded under a condition of 200° C.×5 hours. The physical properties of the cured products obtained are shown in Table 8.

COMPARATIVE EXAMPLE 9

A resin blend comprising 1 mole of BMI and 0.4 mole of diaminodiphenylmethane (hereinafter referred to as DDM) was pressmolded under a condition of 230° C.×5 hours i the same manner as in Example 26, to obtain a cured product. The physical properties of this product are shown in Table 8.

TABLE 8

| Example | | | Example 26 | Example 27 | Example 28 | Comparative example 9 |
| --- | --- | --- | --- | --- | --- | --- |
| BMI (g) | | | 100 | 100 | 100 | 100 |
| Imide compound in Example 1 (g) | | | 117.1 | 87.8 | 122.2 | |
| Sumi ® epoxy ELA-128 (g) | | | | | 11.5 | |
| DDM (g) | | | | | | 22.1 |
| Physical | $T_g$ | °C. | 267 | 266 | 255 | 250 |

TABLE 8-continued

| Example | | | Example 26 | Example 27 | Example 28 | Comparative example 9 |
|---|---|---|---|---|---|---|
| properties of cured product | Expansion coefficient $\alpha_1$* | °C.$^{-1}$ | $4.8 \times 10^{-5}$ | $5.15 \times 10^{-5}$ | $5.2 \times 10^{-5}$ | $4.8 \times 10^{-5}$ |
| | Expansion* (260° C./25° C.) | % | 1.2 | 1.39 | 1.6 | 1.9 |
| | Flexural modulus | kg/mm$^2$ | 452 | 448 | 420 | 410 |
| Gelation time (180° C.) | | min | 12 | 12 | 10 | 20 |

*Measured by the TMA method (by means of DT-40 thermal analyzer; product of Shimadzu Seisakusho Co., Ltd.)
Other measurement values were obtained according to JIS 6911.

What is claimed is:

1. An epoxy resin composition comprising as essential components an epoxy resin (A) and an imide compound (B) represented by the general formula (I),

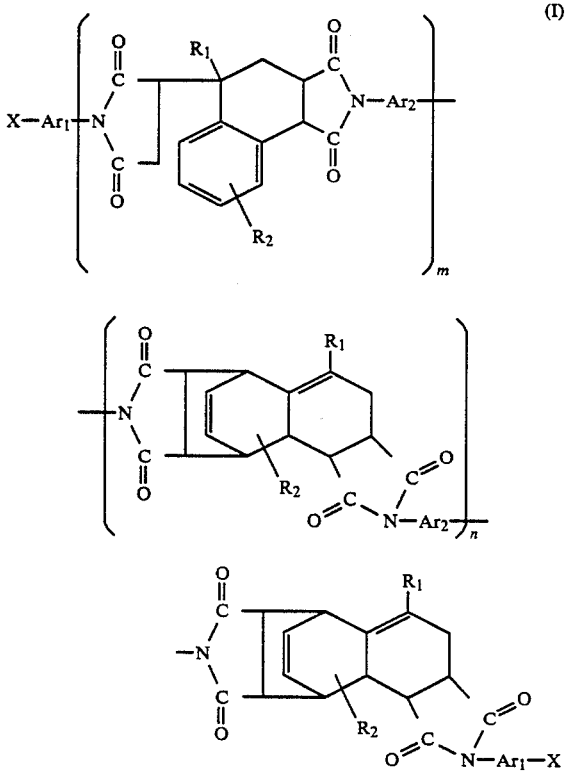

wherein X represents an —NH$_2$ group and/or —OH group, Ar$_1$ and Ar$_2$ independently represent an aromatic residue, R$_1$ represents a hydrogen atom or an alkyl group having from 1 to 10 carbon atoms, R$_2$ represents a hydrogen atom, an alkyl or alkoxy group having from 1 to 20 carbon atoms or hydroxyl group, and each of m and n represents a number of from 0 to 30.

2. An epoxy resin composition according to claim 1, wherein each of m and n represents a number of from 0 to 8.

3. An epoxy resin composition according to claim 1, wherein each of m and n represents a number of from 0 to 5.

4. An epoxy resin composition comprising an epoxy resin (A), an imide compound (B) represented by the general formula (I) and a polymaleimide compound (C) containing two or more maleimide groups in the molecule:

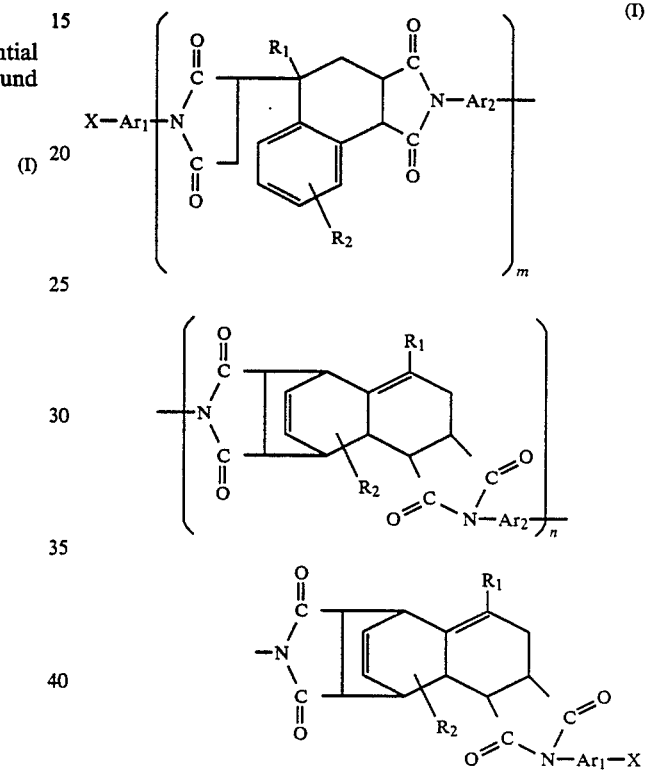

wherein X represents an —NH$_2$ group and/or —OH group, Ar$_1$ and Ar$_2$ independently represent an aromatic residue, R$_1$ represents a hydrogen atom or an alkyl group having from 1 to 10 carbon atoms, R$_2$ represents a hydrogen atom, an alkyl or alkoxy group having from 1 to 20 carbon atoms or hydroxyl group, and each of m and n represents a number of from 0 to 30.

5. An epoxy resin composition according to claim 4, wherein each of m and n represents a number of from 0 to 8.

6. An epoxy resin composition according to claim 4, wherein each of m and n represents a number of from 0 to 5.

7. An epoxy resin composition according to claim 4, wherein the proportion of the epoxy resin (A) and imide compound (B) is such that (B) is from 0.6 to 1.2 gram equivalent per 1 gram equivalent of (A), the proportion of the polymaleimide compound (C) and imide compound (B) is such that the number of active hydrogen atoms H in the terminal functional group X of (B) is from 0.6 to 1 per 1 double bond in (C), and the weight ratio of (A) and (C), i.e. (A)/(C), is from 95/2 to 40/60.

8. An epoxy resin composition according to claim 4 wherein the polymaleimide compound is N,N'- diphenylmethane bismaleimide or N,N'-diphenylether bismaleimide.

9. An epoxy resin composition comprising an epoxy resin (A), an imide compound (B) represented by the general formula (I) and a compound (D) having two or more phenolic —OH groups in the molecule:

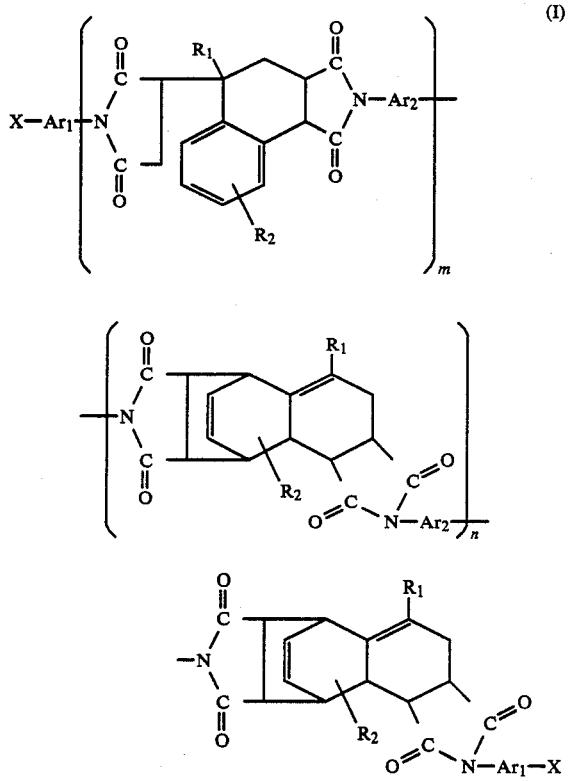

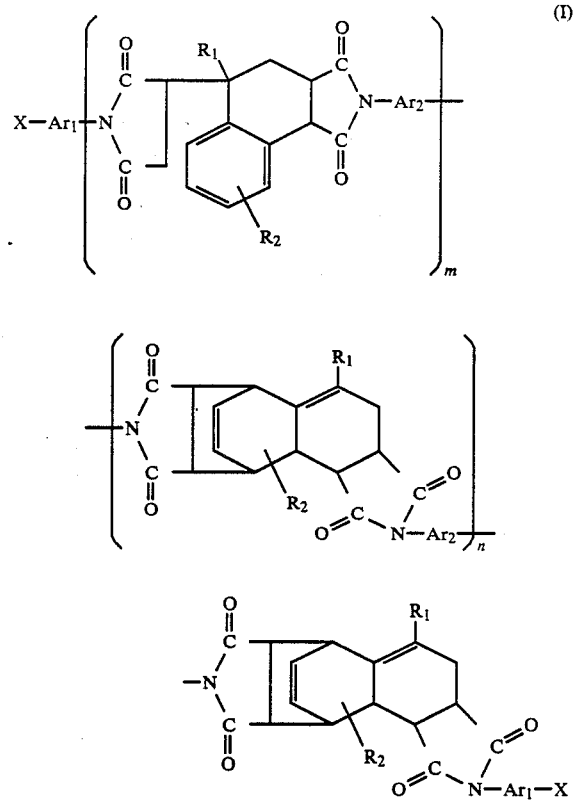

wherein X represents an —NH$_2$ group and/or —OH group, Ar$_1$ and Ar$_2$ independently represent an aromatic residue, R$_1$ represents a hydrogen atom or an alkyl group having from 1 to 10 carbon atoms, R$_2$ represents a hydrogen atom, an alkyl or alkoxy group having from 1 to 20 carbon atoms or hydroxyl group, and each of m and n represents a number of from 0 to 30.

10. An epoxy resin composition according to claim 9, wherein each of m and n represents a number of from 0 to 8.

11. An epoxy resin composition according to claim 9, wherein each of m and n represents a number of from 0 to 5.

12. An epoxy resin composition according to claim 9, wherein the ratio of the number of active hydrogen atoms in the terminal functional groups X of the imide compound (B) and the number of —OH groups in the polyphenol compound (C), i.e. (B)/(C), is from 2/1 to 4/1, and the sum of active hydrogen equivalents in (B) and (C) is from 0.6 to 1.2 gram equivalent per 1 gram equivalent of the epoxy resin (A).

13. An epoxy resin composition comprising an epoxy resin (A), an imide compound (B) represented by the general formula (I), a polymaleimide compound (C) having two or more maleimide groups in the molecule and a compound (D) having two or more phenolic —OH groups in the molecule:

wherein X represents an —NH$_2$ group and/or —OH group, Ar$_1$ and Ar$_2$ independently represent an aromatic residue, R$_1$ represents a hydrogen atom or an alkyl group having from 1 to 10 carbon atoms, R$_2$ represents a hydrogen atom, an alkyl or alkoxy group having from 1 to 20 carbon atoms or hydroxyl group, and each of m and n represents a number of from 0 to 30.

14. An epoxy resin composition according to claim 13, wherein each of m and n represents a number of from 0 to 8.

15. An epoxy resin composition according to claim 13, wherein, each of m and n represents a number of from 0 to 5.

16. An adhesive composition which comprises as essential components an epoxy resin (A) and an imide compound (B) represented by the general formula (I),

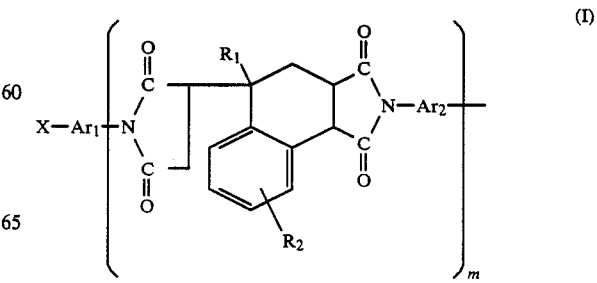

-continued

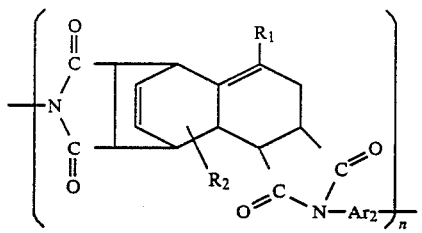

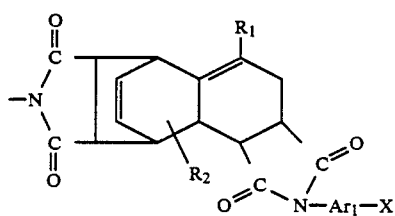

wherein X represents an —$NH_2$ group and/or —OH group, $Ar_1$ and $Ar_2$ independently represent an aromatic residue, $R_1$ represents a hydrogen atom or an alkyl group having from 1 to 10 carbon atoms, $R_2$ represents a hydrogen atom, an alkyl or alkoxy group having from 1 to 20 carbon atoms or hydroxyl group, and each of m and n represents a number of from 0 to 30.

17. An adhesive composition according to claim 16, wherein each of m and n represents a number of from 0 to 8.

18. An adhesive composition according to claim 16, wherein each of m and n represents a number of from 0 to 5.

19. A thermosetting resin composition which comprises a polymaleimide compound having two or more maleimide groups in the molecule and an imide compound represented by the general formula (I),

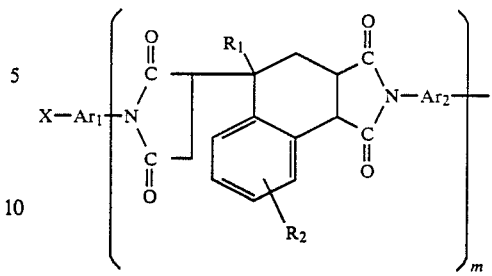

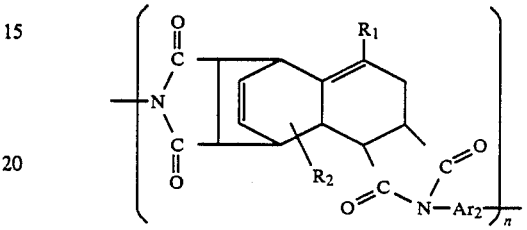

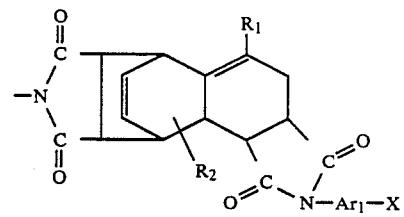

wherein X represents an —$NH_2$ group and/or —OH group, $Ar_1$ and $Ar_2$ independently represent an aromatic residue, $R_1$ represents a hydrogen atom or an alkyl group having from 1 to 10 carbon atoms, $R_2$ represents a hydrogen atom, an alkyl or alkoxy group having from 1 to 20 carbon atoms or hydroxyl group, and each of m and n represents a number of from 0 to 30.

20. A thermosetting resin composition according to claim 19, wherein each of m and n represents a number of from 0 to 8.

21. A thermosetting resin composition according to claim 19, wherein each of m and n represents a number of from 0 to 5.

22. An epoxy resin composition according to claim 7 wherein the polymaleimide compound is N,N'-diphenylmethane bismaleimide or N,N'-diphenylether bismaleimide.

* * * * *